US012622799B2

(12) United States Patent
Laitzsch et al.

(10) Patent No.: US 12,622,799 B2
(45) Date of Patent: May 12, 2026

(54) ORTHOSIS

(71) Applicant: FERD. HAUBER GMBH, Nürtingen (DE)

(72) Inventors: Lukas Laitzsch, Berlin (DE);
Christian Horst, Kirchheim u. Teck (DE); Stephan Blanc, Winterthur (CH);
Timo Schmeltzpfenning, Tübingen (DE)

(73) Assignee: FERD. HAUBER GMBH, Nurtingen (DE)

( * ) Notice: Subject to any disclaimer, the term of this patent is extended or adjusted under 35 U.S.C. 154(b) by 283 days.

(21) Appl. No.: 18/274,287

(22) PCT Filed: Jan. 31, 2022

(86) PCT No.: PCT/EP2022/052167
§ 371 (c)(1),
(2) Date: Jul. 26, 2023

(87) PCT Pub. No.: WO2022/162208
PCT Pub. Date: Aug. 4, 2022

(65) Prior Publication Data
US 2024/0074885 A1 Mar. 7, 2024

(30) Foreign Application Priority Data

Feb. 1, 2021 (DE) ..................... 10 2021 102 282.7

(51) Int. Cl.
*A61F 5/01* (2006.01)
(52) U.S. Cl.
CPC .......... *A61F 5/0127* (2013.01); *A61F 5/0118* (2013.01); *A61F 5/0125* (2013.01)

(58) Field of Classification Search
CPC ........ A61F 5/01; A61F 5/0104; A61F 5/0106; A61F 5/0109; A61F 5/0127;
(Continued)

(56) References Cited

U.S. PATENT DOCUMENTS 5,458,564 A * 10/1995 Franzen .................. A61F 5/013
128/878
5,836,902 A 11/1998 Gray
(Continued)

FOREIGN PATENT DOCUMENTS

DE 10 2018 126990 A1 4/2020
EP 0 774 939 B1 8/2001
EP 3 045 152 A1 7/2016

OTHER PUBLICATIONS

English language Abstract of EP0774939B1.
English language Abstract of DE102018126990A1.
English language Abstract of EP3045152A1.

*Primary Examiner* — Alireza Nia
*Assistant Examiner* — Gina McCarthy
(74) *Attorney, Agent, or Firm* — William J. Barber;
WARE FRESSOLA MAGUIRE & BARBER LLP

(57) ABSTRACT

The invention relates to an orthosis comprising at least one stability-providing structural component having an irregular lattice structure extending over its entire surface. The lattice structure includes webs of strengthening material that delimit irregularly shaped recesses free of structural material. Within the planar extension of the structural component, a stabilization direction (S) is defined along which the component exhibits stabilizing flexural rigidity, and an adaptation direction (A) orthogonal thereto along which the component is locally bendable.

20 Claims, 16 Drawing Sheets

(58) Field of Classification Search
CPC .... A61F 5/0118; A61F 5/0123; A61F 5/0125;
A61F 5/0102; A61F 5/013; A61F
5/05841; A61F 5/3715; A61F 2005/0146;
A61F 2005/0158; A61F 2005/0167; A61F
13/08
See application file for complete search history.

(56) References Cited

U.S. PATENT DOCUMENTS

| | | | |
|---|---|---|---|
| 2006/0030802 A1* | 2/2006 | Nordt .................. | A41D 13/065 |
| | | | 602/26 |
| 2009/0076426 A1 | 3/2009 | Einarsson et al. | |
| 2018/0228635 A1* | 8/2018 | Lê ......................... | A61F 5/0118 |
| 2020/0345530 A1* | 11/2020 | Natsis .................. | A61F 5/0127 |
| 2021/0393430 A1 | 12/2021 | Schilling et al. | |

\* cited by examiner

E-E

F-F

S

S

S

150

ORTHOSIS

The present invention relates to an orthosis. Conventionally, orthoses are manufactured in a variety of different sizes to meet the requirements of various wearers.

In particular, the production of stability-providing structures, i.e., of stability-providing parts of the orthosis or the individual parts thereof (hereinafter referred to as structural components), plays a decisive role. These are frequently produced as metal or plastic parts, and the production of different sizes requires the use of various tools. For example, in conventional orthoses, the structural components of which are produced by means of injection molding, a different injection molding tool must be used for each size of the orthosis. This leads to high tool costs. On the other hand, the differences in the dimensions of the orthoses of individual sizes cannot be selected to be arbitrarily large, because otherwise a correct seating of the orthosis cannot be ensured.

The object of the present invention is to provide an orthosis which can be used by as wide a variety of wearers as possible.

To solve this problem, the present invention proposes an orthosis which has a stability-providing structural component with high adaptability and at the same time sufficient stabilization. Such an orthosis is defined, for example, in claim 1. Further embodiment variants of the orthosis according to the invention are described in the following description and dependent claims.

The orthosis comprises a stability-providing structural component. The structural component comprises a strengthening structural material or may consist thereof.

The stability-providing structural component can have an irregular lattice structure over its entire surface. The irregular lattice structure has webs of strengthening structural material and the webs delimit irregularly shaped recesses free of structural material. In stabilizing regions, the webs can be made thicker than in adaptable regions. In particular, the predominant portion or all of the webs can be formed in stabilizing regions with a material thickness at least twice as thick as a predominant portion or all of the webs in the adaptable regions.

The structural component is planar. Planar in this context means an embodiment of the structural component in which the thickness of the structural component in the direction of the local surface normal is significantly lower than the dimensioning of the structural component along its planar extension. However, a planar extension does not mean the extension in a geometric plane; instead, the structural component can have a three-dimensionally sweeping or curved shape. Typically, the structural component is formed complementary to the limb or body shape to be supported in an area surrounding a joint.

The structural component can have at least one stabilization direction lying in the planar extension. Transverse to the stabilization direction, the structural component is designed with local flexural rigidity (in a region of the structural component) to have a stabilizing effect. In the applied state of the orthosis, the structural component is arranged such that the stabilization direction of the structural component runs along the body of the wearer, so that the wearer's body part to be stabilized is stabilized by the structural component. A bending transverse to the stabilization direction is possible only to a minimal degree. The structural component is thus designed to be rigid transverse to the stabilization direction, such that it serves to support or stabilize a limb of the orthosis wearer (in the applied state). Having stabilizing flexural rigidity is understood in this context to mean a flexural rigidity which can permit a certain bending, as is customary in a rail of an orthosis, but in any case is small enough that the supporting function and stabilization of the limb is performed.

In addition to the stabilization direction, the structural component can have an adaptation direction lying in the planar extension. The structural component is designed to be locally bendable in relation to the adaptation direction. In this case, the structural component is designed to be bendable transversely to the adaptation direction such that it can be brought into planar contact with the contour of a limb of an orthosis wearer by bending transversely to the adaptation direction. The bending necessary for this can be achieved manually during the application. For example, the orthosis or its structural component (s) can be fixed by corresponding fastening straps and at the same time be adapted, by bending, to the local body shape of the wearer. The fastening and adaptation by means of the fastening straps also contributes to the secure seating of the orthosis. Although the structural component is bendable transverse to the adaptation direction, it offers in particular a certain resistance to a bending, so that it maintains a tension when applied.

The discussed bendings of the structural components as provided by this invention refer to a bending in the direction of the local surface normal to the extension of the structural component. The local stabilization direction and the local surface normal thus span a stabilizing plane (a plane in the geometric sense). The structural component is flexurally rigid in flexurally rigid regions such that its cross section in this stabilizing plane remains almost unchanged under load. The local adaptation direction and the local surface normal span an adaptation plane (a plane in the geometric sense). The structural component is flexible in adaptable regions such that its cross section in this adaptation plane changes under load and, in particular, can be adapted to different body shapes of different wearers.

The orthosis therefore comprises at least one structural component which is designed to be sufficiently stiff transverse to the stabilization direction for stabilizing a body part of the wearer and, in contrast to this, is designed to be locally flexible transverse to the adaptation direction in such a way that it can be adapted to different body sizes.

For example, a wrist orthosis according to the invention can be adapted to different hand sizes or arm diameters, or a knee orthosis according to the invention can also be adapted to different leg diameters. The adaptation takes place here by the bendable and flexible configuration of the structural component transverse to the adaptation direction when the orthosis is applied, for example by tensioning and fastening by means of fastening strap or fastening straps. A tool-assisted adaptation, for example, by adjusting corresponding angles and varying a diameter is not necessary in the orthosis according to the invention. The lattice structure of the structural component already described in the introduction represents an option for designing the structural component that is easy to produce, by means of which the desired properties can be reliably provided. In particular, a specific selection of the placement and dimensioning of individual webs and a variation of the number of webs advantageously achieve a local adjustment of the stiffness of the structural component over its planar extension. As a result, individual regions of the structural component can be designed to be flexurally rigid and other regions can be designed to be flexible. Various local stiffnesses and degrees of flexibility are easily realizable.

The lattice structure has in particular a closed edge. Thus, no webs terminate in the edge in the direction of their longitudinal extension. Rather, the edge is formed by a circumferential web.

The recesses that are free of material have in particular a plurality of different shapes, in particular at least 3, in particular 5, in particular 7, different shapes of recesses on a structural component. In particular, the recesses are formed predominantly or exclusively with rounded corners. In the direction of connection points with further webs, the inserts can thicken in the planar extension of the structural component. In particular, there are different connection points in a structural component, in particular connection points in which a web impinges on a web extends in a straight line, connection points in which a plurality of webs impinge on a web which extends in a straight manner and connection points in which a plurality of (in particular 3 to 6, in particular up to 5) webs from different directions intersect. The structural component can comprise connection points in which 2 straight-extending webs intersect. The different connection points can be present in different combinations in the structural components.

The structural component can in particular have one or more stabilizing regions and one or, in particular, more adaptable regions. In particular, the structural component can comprise adaptable regions which are each arranged next to a stabilizing region in the view along the stabilization direction in this stabilizing region.

The structural component can in particular have a partially flexible region 244; in such a partially flexible region, the structural component has stabilization directions and adaptation directions running at an angle of at least 45° relative to one another, in particular of at least 65°, in particular of at least 80° relative to one another.

The stabilization directions in particular indicate the directions with the greatest stiffness, and the adaptation directions in particular with the greatest flexibility.

For example, an increased number of webs can be provided in the stabilizing region around the stabilization direction in order to achieve a stabilizing effect. It is also possible to provide webs in the stabilizing region with a higher material thickness, in particular transverse to the stabilization direction. In particular, the webs can also be designed to extend predominantly in the stabilization direction.

Accordingly, in the adaptable region the webs can run extending predominantly transversely to the adaptation direction. For this purpose, the predominant number of webs can run transversely to the adaptation direction or their direction is predominantly transverse to the adaptation direction (at a small angle to the adaptation direction). The webs in the adaptable region can also have a smaller material thickness than the webs in the stabilizing region. The spatial density of the webs can be selected to be smaller in the adaptable region than in the stabilizing region. The various ways of achieving an adaptability or flexibility and a stiffness can be applied individually or in combination with one another.

As mentioned, the orthosis may comprise one or more fastening straps. The fastening strap has in particular a planar design. In its width and in its length, it can have a substantially larger extension than in its material thickness for these two directions. It can be manufactured from a pliable material. It can have an inelastic design.

In particular, the structural component can be connected to at least one fastening strap. The fastening strap can be non-detachably attached to the structural component. In particular, the fastening strap can indeed be mounted displaceably with respect to the structural component, but connected non-detachably thereto. The fastening strap or the fastening straps can also be designed to be fixable on itself by means of a hook-eye material connection and extend through an eyelet or a slot or other recess in the structural component or the stability-providing structure of the orthosis. The fastening strap can comprise an unthreading stop, in particular in the form of a plastic component which is non-detachably connected to the pliable material of the fastening strap. In particular, the unthreading stop can be a plastic ring which is connected to the material of the fastening strap in particular by ultrasonic welding.

The fastening strap can be fastened to the structural component in a fixed extension direction and can be designed for the circular wrapping of the limb of the orthosis wearer that is to be stabilized by the orthosis. In particular, it can be provided that the fastening strap is fastened at one of its ends to a feedthrough on the structural component and extends away therefrom. Furthermore, a free end of the fastening strap opposite the fastened end can extend through a further feedthrough. To fasten the orthosis, the free end of the fastening strap can be fixed to itself by means of a hook-eye connection, for example a hook-and-loop fastener. The wrapping of the limb can be formed by the fastening strap itself (wraps around the entire circumference of the limb) or by the fastening strap and at least one structural component.

The orthosis can comprise at least two structural components which are each integrally formed in one piece. The at least two structural components can be arranged separately from one another or connected to one another on the orthosis.

The structural components can, for example, be pivotably connected to one another via an articulation. Typically, such an articulated connection between the structural components allows a change in the position of the structural components transversely to a respective stabilization direction of the structural components.

The at least two structural components can be connected to one another by means of a connecting device in a position and orientation fixed relative to one another and can be fixed with respect to one another (fixed in position and orientation relative to one another).

The orthosis can comprise a pliable padding component on a side of the structural component provided for contacting the limb of the wearer. The padding component can be detachably or non-detachably connected to the structural component. In particular, the padding component can be inserted into the structural component. The structural component can have, for example, hole-like perforations, and the padding component can have clip connections designed to be complementary thereto.

The structural component can in particular be produced as one-piece injection-molded parts. In particular, it can be provided that the structural component is formed without undercuts in order to ensure a simple demolding.

For the purposes of the present invention, the orthosis is in particular an ankle orthosis. The ankle orthosis preferably has, on the distal side, two shell elements formed for contacting the foot respectively on the lateral and foot sole sides, said shell elements having a connection portion aligned in the proximal direction with respect to the arrangement parallel to the foot sole of a wearer. An articulation preferably adjoins the support portion. A structural component is connected to this articulation on each of the shell elements, which structural component is pivotably connected to the respective shell element by the articulation. The respective structural components are preferably curved so that they substantially follow the contour of the lower leg of a wearer. Furthermore, the structural component is preferably designed such that it is flexibly adaptable in this curvature, i.e., designed to be adaptable to different lower leg circumferences of a wearer. At the same time, however, the structural component is designed so as to be rigid in such a way that a bending transversely to the distal proximal axis is not possible or only minimally possible. In order to be adaptable as flexibly as possible to different foot widths of a wearer, the two shell elements can be detachably connected to one another via a detachable connection, which is preferably designed in the form of a hook-eye material (hook-and-loop fastener). As a result, the relative position of the two shell elements can be adapted to the foot width of the wearer by reducing or increasing the overlap of the two connecting portions. As a result, the articulation which connects the shell elements to the respective structural components can also be placed as close as possible to the ankle joint.

The orthosis is, in particular, an ankle orthosis and has two shell elements on the distal side which are each designed for laterally contacting a wearer's foot and can be fixed to one another in a variable position, the shell elements being pivotably connected to a respective structural component by means of an articulation arranged proximally to the shell elements, the structural component extending in the proximal direction from the articulation. The structural component extending in the proximal direction from the articulation can comprise a central stabilizing region running in the distal-to-proximal direction, the stabilization direction of which can extend in the distal-to-proximal direction. The orthosis can further comprise adaptable regions arranged laterally from the stabilizing region when viewed in the distal-to-proximal direction. The adaptation direction thereof can run in the circumferential direction of the lower leg of the wearer in the applied state.

For the purposes of the present invention, the orthosis can in particular also be a wrist orthosis.

Such a wrist orthosis in particular has a wrist support portion which can be formed, for example, by a first structural component. Furthermore, the wrist orthosis can have a finger rest which can be designed as a second structural component. Furthermore, the wrist orthosis can alternatively or additionally also comprise a thumb rest, which can be designed as a third structural component.

It is also possible for the wrist orthosis to comprise only a wrist support portion and the associated thumb rest. In this case, the individual fingers are then freely movable and are not supported by the wrist orthosis. As already stated, the described units (wrist support portion, finger rest, thumb rest) of the wrist orthosis can be designed as individual structural components which will be connected or are connected to one another in order to form a stabilizing structure. It is also possible to produce the individual units (wrist support portion, finger rest, thumb rest) together in a structural component.

The structural component forming the wrist support portion or the part of a structural component forming the wrist support portion preferably has a stabilizing region extending from proximal to distal, which region extends in the intended applied state up to the wrist (coming from the proximal direction). Preferably, when viewed in the distal direction to the left and right of the stabilizing region, curved adaptable regions are arranged in a circumferential direction and are flexibly adaptable to the arm diameter of the wearer.

The different flexibilities or stiffnesses or adaptability of the structural components or of the stability-providing structure are preferably realized by different diameters of webs of the lattice structure of the structural components or stability-providing structure. In the stabilizing region extending from proximal to distal, the stabilization direction runs from proximal to distal in the surface of the structural component. The structural component is designed such that it is arranged on the side of the palm in the applied state. Depending on the side of the stabilizing region, curved adaptation regions can be provided which can be adapted in their curvature in order to be adapted to the arm diameter of the wearer. In the arm circumferential direction, the stabilizing region and the curved adaptation regions have in particular an approximately identical extension, the adaptation regions each having a maximum extension that is 1.5 times, in particular 1.3 times, the extension in the arm circumferential direction. This relates to the part of the structural component extending proximally from the wrist, in the applied state.

For the purposes of the invention, the orthosis can in particular also be a knee orthosis. The knee orthosis has a stability-providing structure which comprises a plurality of structural components connected to one another in an articulated manner.

A proximal portion of the stability-providing structure is pivotably connected to a distal portion on both sides at the height of the knee joint (in the applied state). Both the proximal and the distal portion can in turn comprise at least two structural components. The structural components can in particular be adapted to one another in their position via a distal and proximal articulation. The proximal and the distal articulation allow a pivoting movement about an axis, which axis runs orthogonally to the knee pivot axis or to the pivot axis of the articulations at the level of the knee which connect the proximal portion to the distal portion.

These articulations can be used to adapt the inclination of the portions to the structural components that run parallel to the wearer's leg. Thus, the inclination of the portions of the structural components running proximal-to-distal. In order to be able to structurally compensate for this inclination adaptation, the respective structural components have a bendable adaptable region which is spaced apart from the respective articulation by a stabilizing region at the height of the knee joint. The structural components can have the above-described lattice-like structure with webs and recesses free of structural material. The flexibility in the adaptable region can in particular be caused by an increased spacing and/or a thinner design of the webs. Likewise, the bendability in the adaptable region can be brought about by the webs having an overall orientation which runs more in the direction of a bending axis about which the structural component is bendable in the adaptable region than in the stabilizing region. The three mechanisms for achieving an increased or reduced degree of flexibility can also be applied in a superimposed manner.

The invention is described in more detail below with reference to the drawings, the same or functionally equivalent elements being provided only once with reference signs if necessary. In the drawings:

FIG. 1 shows an ankle orthosis in a front view;
FIG. 2 shows the ankle orthosis in a rear view;
FIG. 3 shows the ankle orthosis in a side view;
FIG. 4 shows a part of the ankle orthosis in a perspective view;
FIG. 5 shows a part of the ankle orthosis in a perspective view;
FIG. 6 shows a part of the ankle orthosis;

7
8

Figures 1, 2, 3:
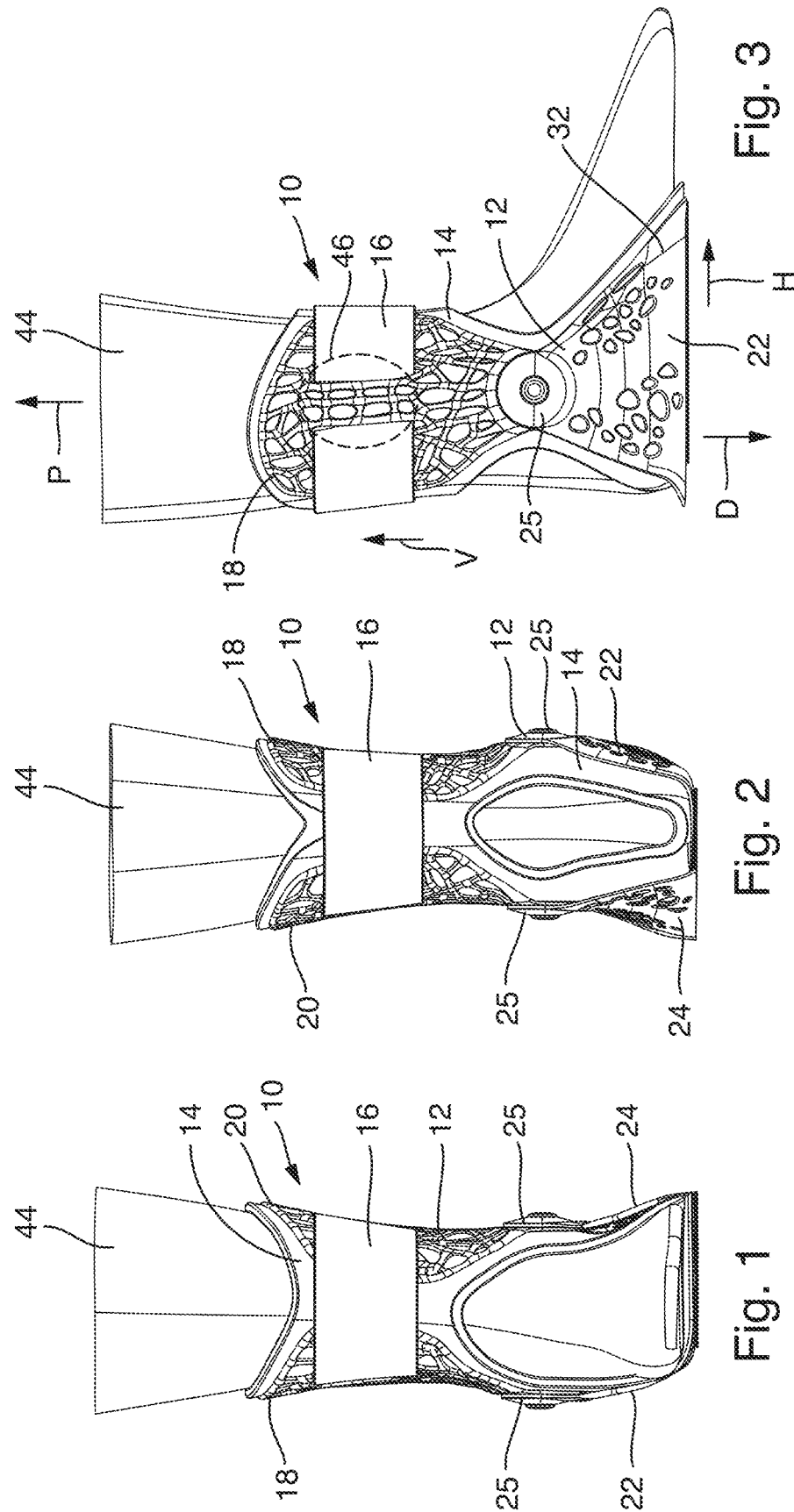
Figure 5:
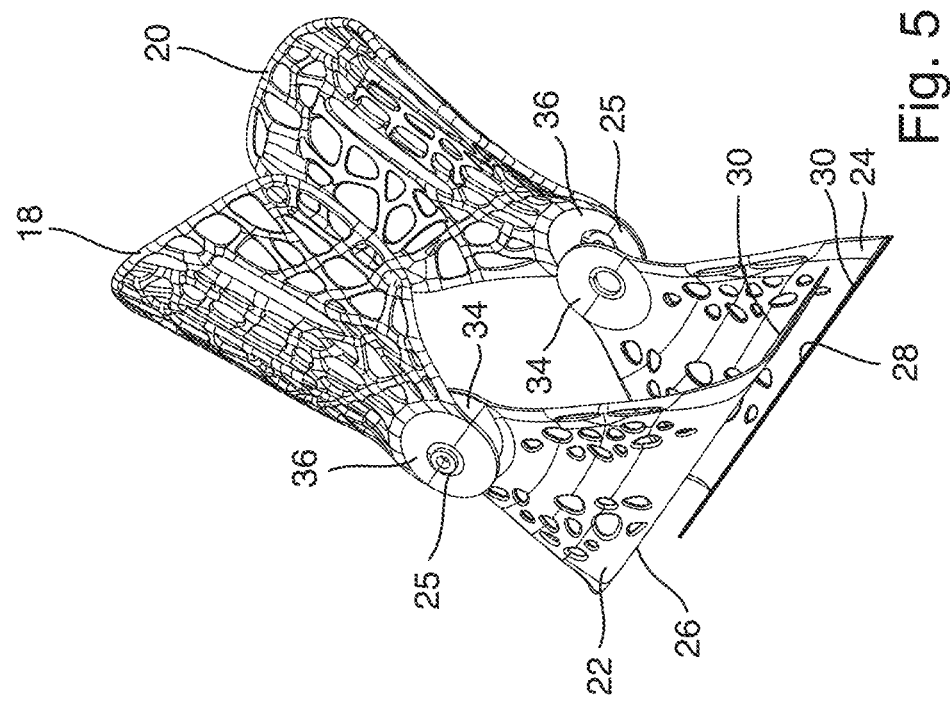
Figure 4:
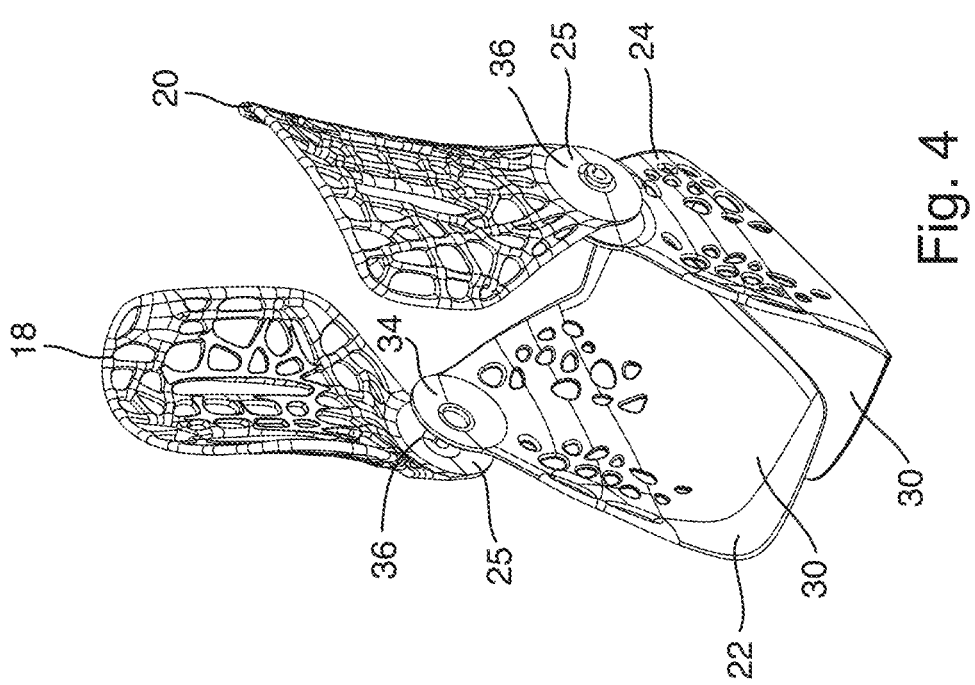

FIG. 1 shows a front view of an orthosis 10 according to the invention, which orthosis is designed as an ankle orthosis 10. The ankle orthosis 10 comprises a stability-providing structure 12, a padding component 14 and a fastening strap 16. The ankle orthosis 10 is shown in FIG. 2 in a rear view and in FIG. 3 in a side view. FIGS. 4 and 5 show the stability-providing structure 12 of the ankle orthosis 10 in each case without the padding component 14 and the fastening strap 16. The fastening strap 16 is designed for the circular wrapping of a body part, in the present case a leg 44 of the wearer. For this purpose, it is guided through a loop 46 of the stability-providing structure 12.

The stability-providing structure 12 comprises a first structural component 18 and a second structural component 20. The two structural components 18, 20 are each pivotably connected to a first and second shell element 22, 24 via a respective articulation 25.

The two shell elements 22, 24 can be secured via a hook-eye connection in a fixed position relative one to one another. For this purpose, the first switching element 22 has a hook-eye material (hook-and-loop fastener) on an underside 26 and the shell element 24 on an upper side 28 of a respective connecting portion 30. In the wearing position of the ankle orthosis 10 in the case of a stationary user, as shown for example in FIGS. 1-3, the connecting portions 30 are each extended in the horizontal plane or in the horizontal direction H and are oriented approximately at right angles to supporting portions 32 of the respective shell elements 24. The support portions 32 extend away approximately in the vertical direction V or from the respective articulation 25 in the proximal direction P. In relation to the body directions, the connecting portions 30 are located at the distal end (distal direction D) of the shell elements 24 and the supporting portions 32 extend therefrom in the proximal direction P. The articulations 25 are arranged at the proximal end of the shell elements 24. Accordingly, the articulations 25 are arranged at the distal end of the structural components 18 and 20. In each case, a component 34 of the respective articulation 25 close to the body is arranged on the respective shell element 24 and a component 36 of the articulation 25 facing away from the body is arranged on the respective structural component 18 or 20.

Figure 6:
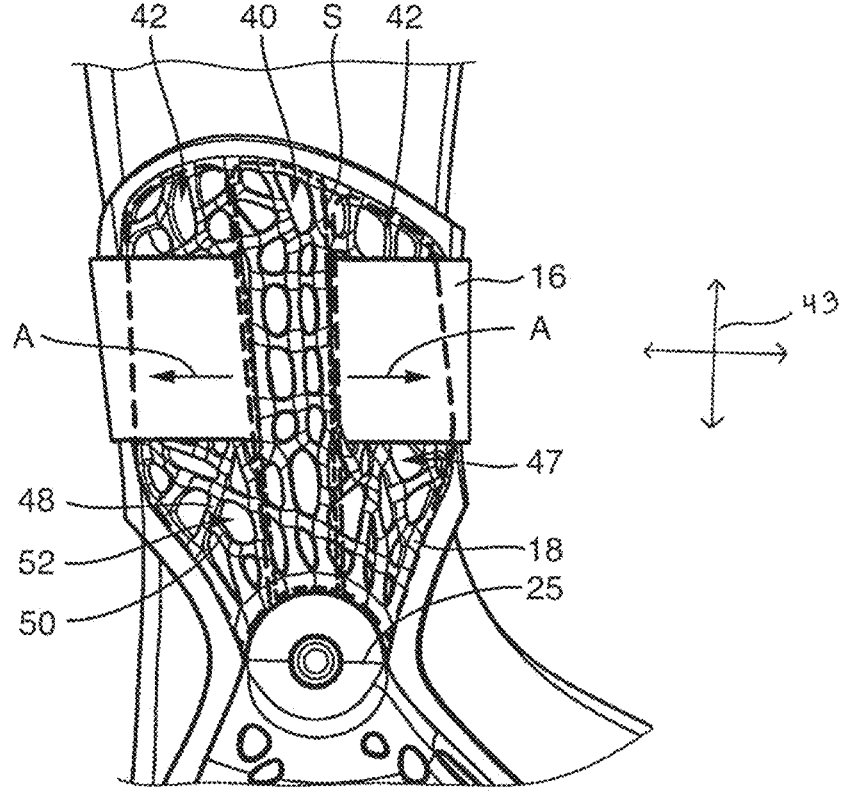

FIG. 6 shows an enlarged detail of structural component 18. The structural component 18 has a stabilizing region 40 which is bordered by a dotted line. A stabilization direction S is indicated by an arrow. In the view along the stabilization direction S, regions 42 which can each be adapted laterally are arranged next to the stabilizing region 40. In the respective adaptable regions 42, respective adaptation directions A are indicated by corresponding arrows. The stabilization direction S and the adaptation direction A are each located in the planar extension of the structural component 18.

Transverse to the stabilization direction S, the structural component 18 is designed to have stabilizing flexural rigidity. In contrast to the adaptation direction A, the structural component 18 is designed to be locally bendable. The two adaptable regions 42 can be varied in their curvature around a leg 44 of a wearer. The ankle orthosis 10 can thereby be adapted to the contour of the leg 44. The ankle orthosis 10 may, for example, be expanded to be applied to a larger diameter leg 44.

The structural component 18 has an irregular lattice structure 47 over its entire surface. The irregular lattice structure 47 comprises webs 48 made of strengthening structural material. The webs 48 delimit irregularly shaped recesses free of structural material 52.

In the stabilizing region 40, the webs 48 are made thicker than in the adaptable regions 42. In particular, the predominant part of the webs 48 in the stabilizing region 40 is formed with a material thickness at least twice as thick as a predominant part of the webs 48 in the adaptable regions 42.

Figure 7:
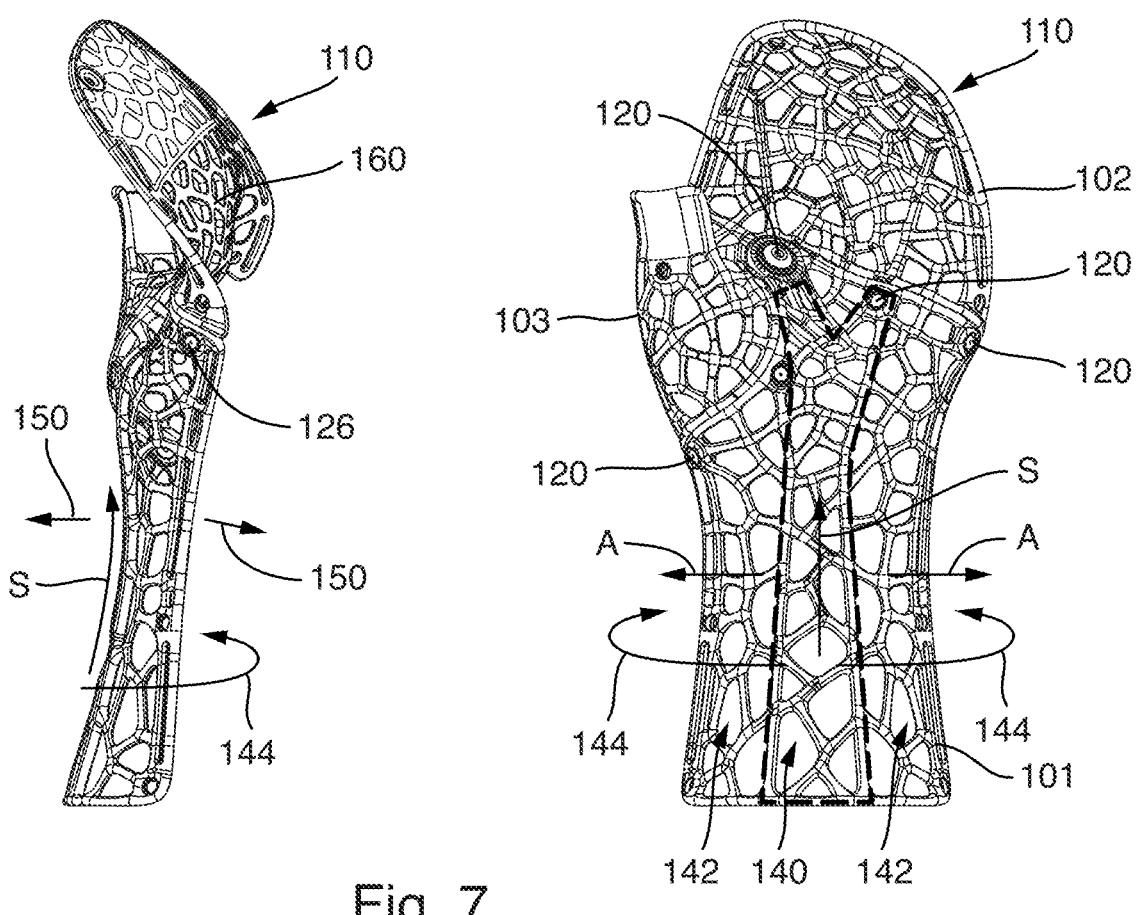
FIG. 7 shows a plurality of interconnected structural components of a wrist orthosis in further views.

FIG. 7 shows a plurality of structural components 101, 102 and 103 connected to one another, which form a stabilizing structure 112 of an inventive wrist orthosis 110 according to the invention. On the left in FIG. 7, a lateral view of the stability-providing structure 112 is shown, and a view of the stability-providing structure 112 is shown on the right when viewing the side facing away from the surface 160 for contacting the hand.

Figure 10:
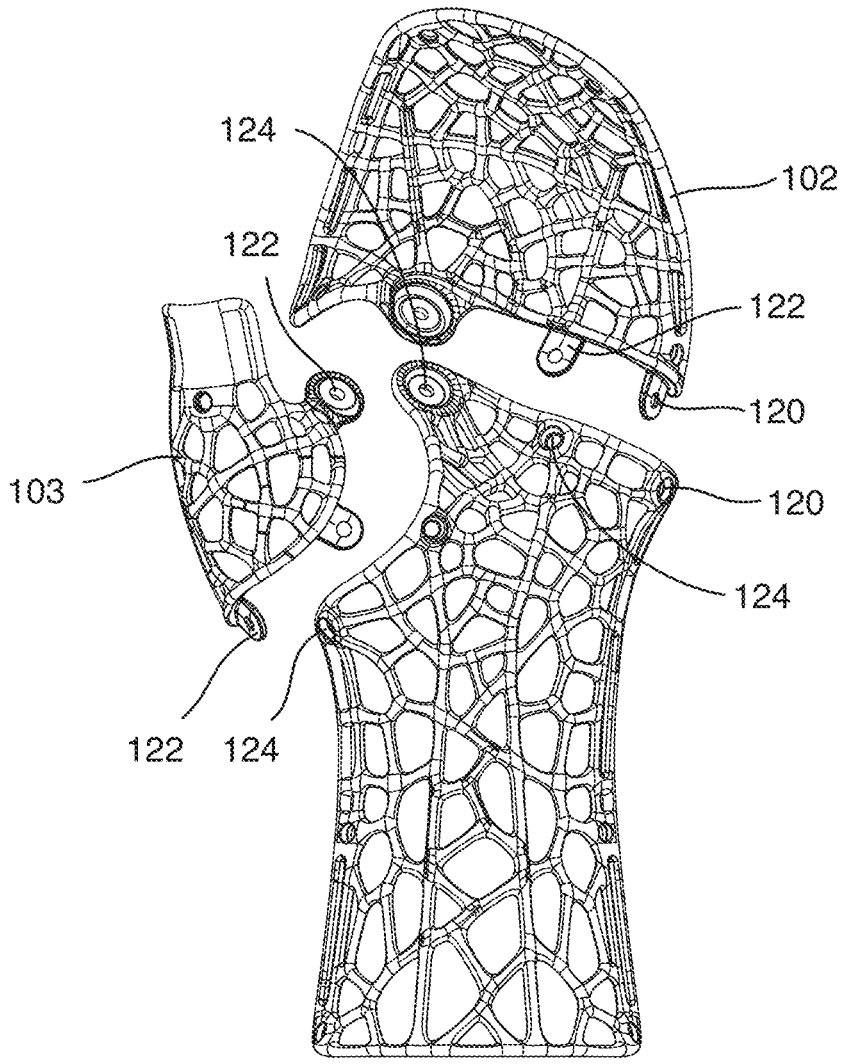
FIG. 10 shows the structural components of the wrist orthosis in a further view in the state detached from one another.

The first structural component 101 is designed to stabilize the wrist of a wearer. A second structural component 102, which is designed as a finger rest, is attached to the first structural component 101. Likewise, a third structural component 103 (thumb rest) is connected to the two other structural components 101, 102. The structural components 101, 203 are connected to one another via connecting devices 120. In FIG. 10, the structure of the connecting devices 120 used in this example can be clearly seen. The second and third structural components 102, 103 each have extensions 122 which are arranged in the connected state so as to overlap with corresponding recesses 124. By means of a rivet, which forms part of the connecting devices 20, or another fixing element 126, the individual structural components 101, 102, 103 are fastened to one another in the connected state.

Figure 8:
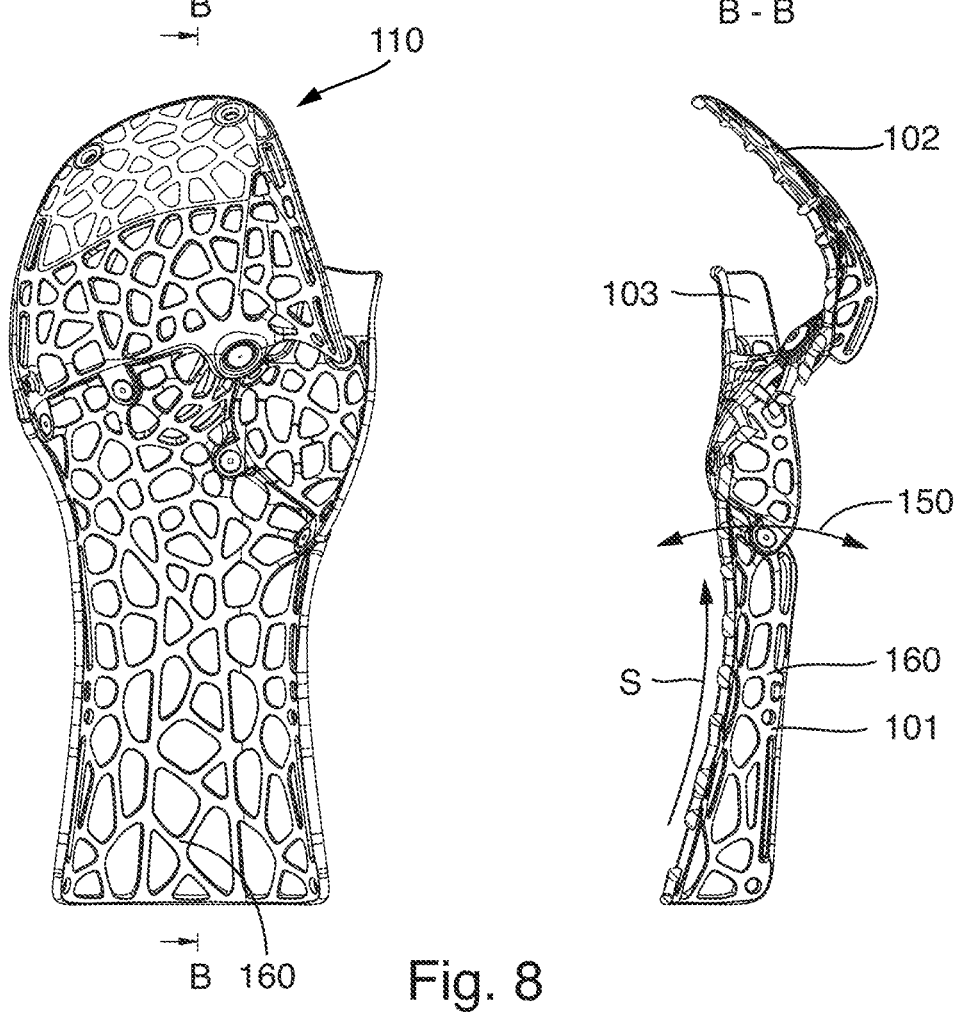
FIG. 8 shows the structural components of the wrist orthosis in a further view and along a section line B-B.
Figure 9:
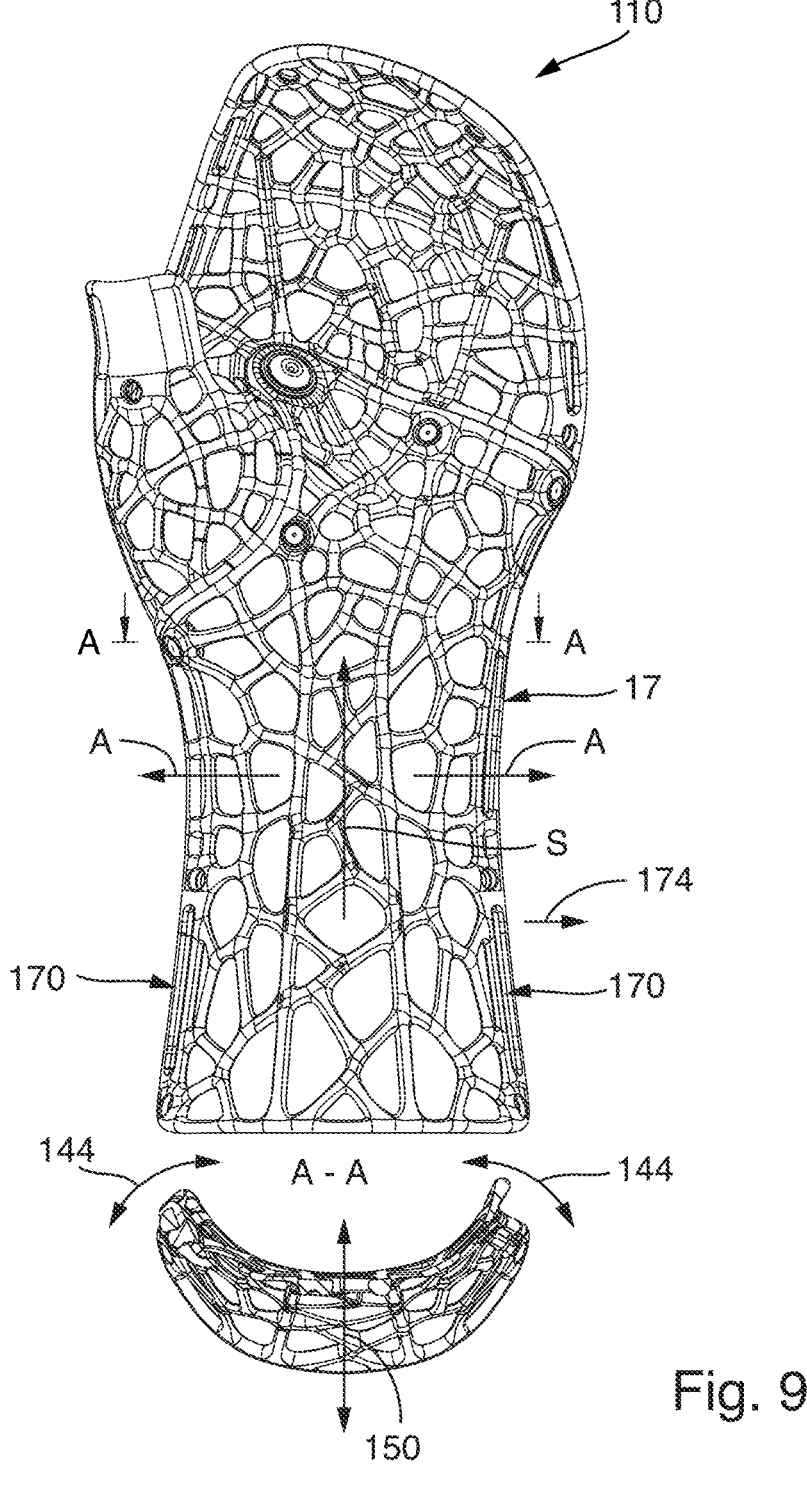
FIG. 9 shows the structural components of the wrist orthosis in a further view and along a section line A-A.

The first structural component 101 fulfills the main function of the stability-providing structure 112. It stabilizes the wrist of the wearer. The stabilization direction S and the adaptation direction A are illustrated on this structural component 101. In the adaptation regions 142, which are each arranged next to the stabilizing region 140 when viewed along the stabilization direction S, the structural component 101 can be flexibly adapted in its curvature, which is illustrated by the curved arrows 144. In the stabilizing region 140, the structural component 101 is designed to have stabilizing flexural rigidity transverse to the stabilization direction S. In the left view of FIG. 7, the directions orthogonal to the stabilization direction S, in which bending of the orthosis is only minimally possible, are indicated by arrows 150. The stabilization direction S and the direction in which no bending or only slight bending of the structural component 101 is possible are also illustrated in FIGS. 8 and 9. The same applies to the adaptation direction A and the bending directions of the structural component 101.

FIG. 8 shows the stability-providing structure 112 from FIG. 7 in a representation (left) when viewing the surface provided for receiving the hand. FIG. 8 further shows a section along the line B-B through the stability-providing structure 112. FIG. 9 shows a view corresponding to the right view of FIG. 7, and a section along the line A-A, which is shown in the lower region of FIG. 9. FIG. 9 clearly illustrates how an unbendability or minimum bendability along the arrow 150 can exert a stabilizing effect on the wrist of the wearer and an adaptation with respect to the thickness of the arm of the wearer is made possible by a bendability of the stability-providing structure 112 in the direction of the arrows 144.

The structural component 101 has an irregular lattice structure 147 over its entire surface. The irregular lattice structure 147 comprises webs 148 made of strengthening structural material. The webs 148 delimit irregularly shaped recesses free of structural materials 152.

Figure 11:
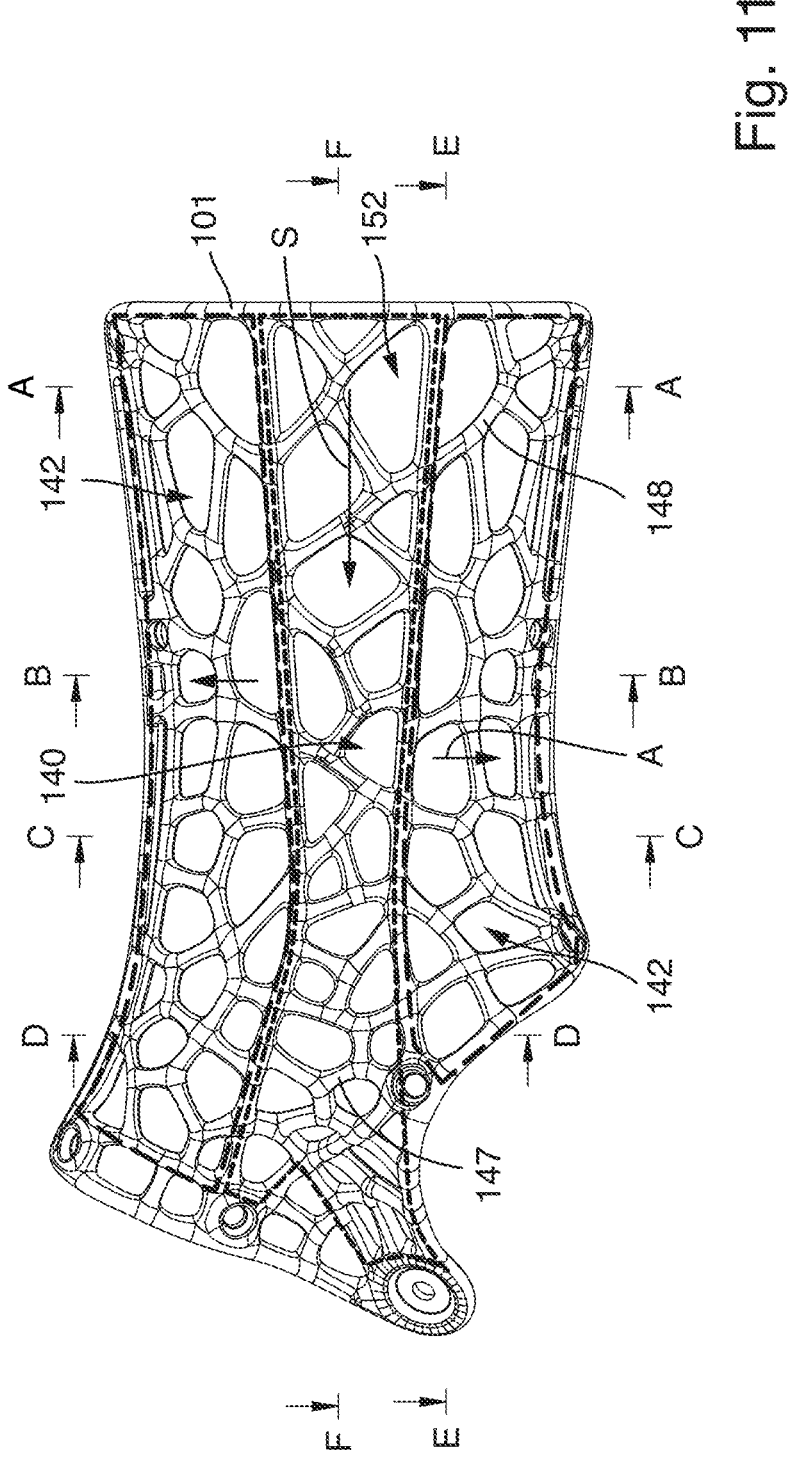
FIG. 11 shows one of the structural components of the wrist orthosis in detail and a plurality of section lines.
Figure 12:
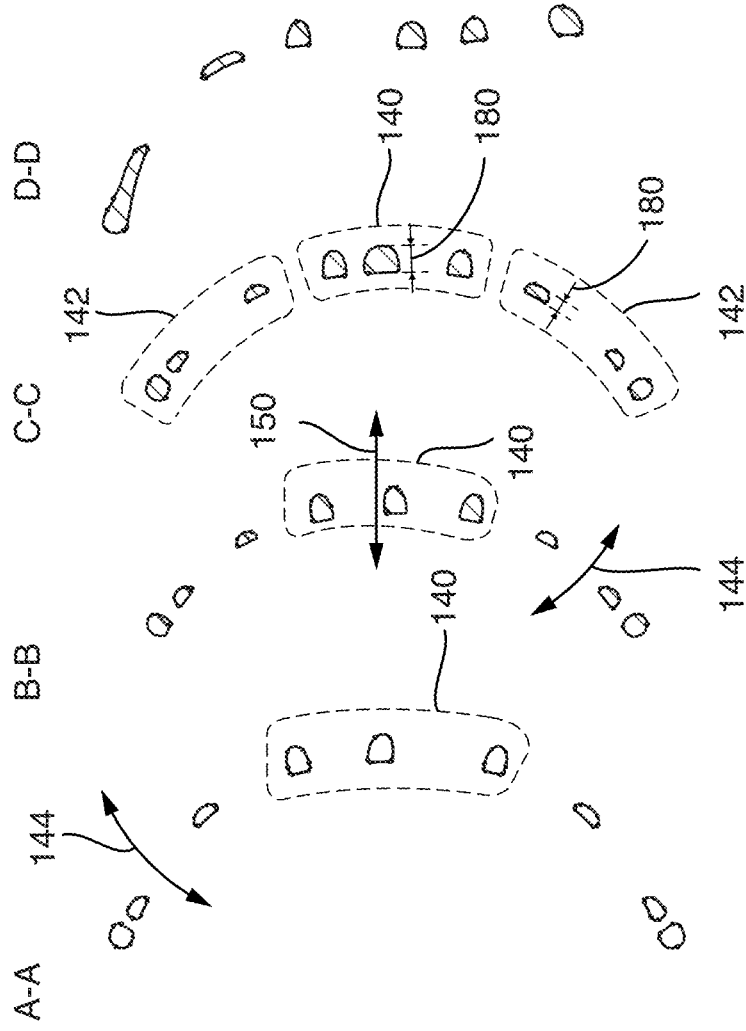
FIG. 12 is a sectional view of the structural component from FIG. 11.
Figure 13:
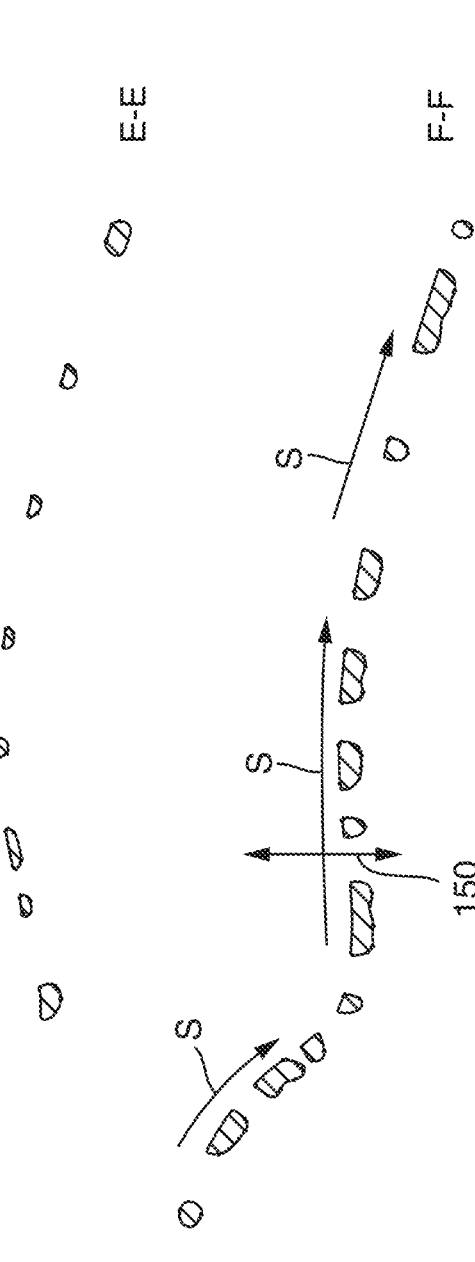
FIG. 13 is a sectional view of the structural component from FIG. 11.
Figure 13:

As shown in FIG. 9, the stability-providing structure 112 has a plurality of slots 170 and 172, which are designed to receive a corresponding fastening strap. Two slots 170 arranged opposite one another are provided at the level of the slots 170. A fastening strap 116 can be fastened in one of the slots in a fixed extension direction 174. The fastening strap 116 is guided around the arm of the wearer and is guided through the opposite slot 170 and from there is guided back onto itself. By means of hook and loop connections attached to the fastening strap 116, the stability-providing structure 112 can thus be ideally adapted to the body shape of the wearer. The fastening of a fastening strap 116 is also provided on the slot 172. However, the fastening strap 116 on this individual slot 172 is provided for wrapping around the arm of the wearer; the fastening strap 116 is thus guided back onto itself. FIG. 11 shows the structural component 101 individually and a plurality of section lines are shown, the sections of which are shown in FIGS. 12 and 13. FIGS. 12 and 13 clearly show that the structural component 101 has webs 148 with a different material thickness 180.

In the stabilizing region 140, the webs 148 are made thicker than in the adaptable regions 142. In particular, the predominant part of the webs 148 in the stabilizing region 140 is formed with a material thickness 180 at least twice as thick as a predominant part of the webs 148 in the adaptable regions 142.

Figure 14:
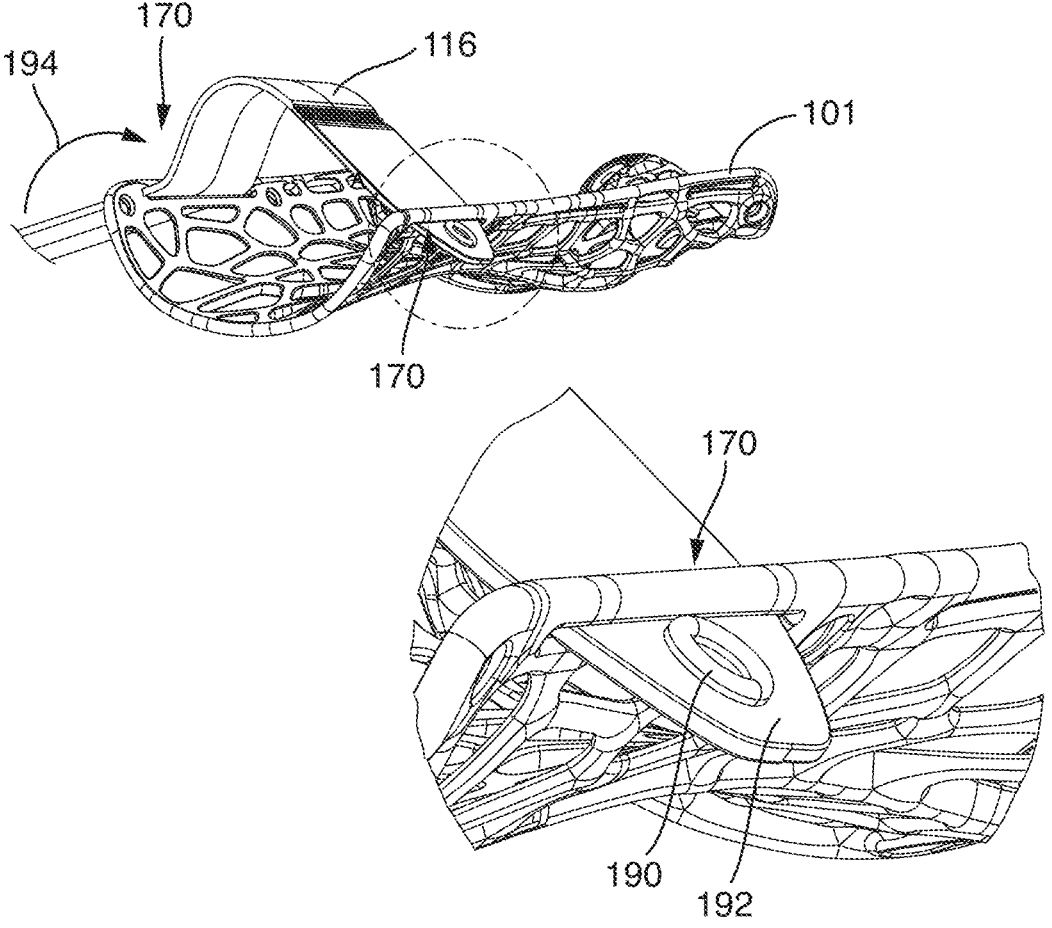
FIG. 14 shows the structural component of the wrist orthosis with a fastening strap mounted thereon.

FIG. 14 shows a fastening strap 116 being guided through the slots 170. The fastening strap has an unthreading stop 190 at its free end 192. The unthreading stop 190 is a ring made of a plastic that is fastened by means of ultrasonic welding to the pliable material of the fastening strap 116. Other forms are also within the meaning of the invention. To fix the fastening strap 116 on the side opposite the unthreading stop 190, the fastening strap 116 is guided back onto itself in order to capture the perimeter of the slot 170, which is illustrated by the arrow 194. For this purpose, the fastening strap 116 has a hook-eye material (hook-and-loop fastener) on its surface.

Figures 15, 16, 17:
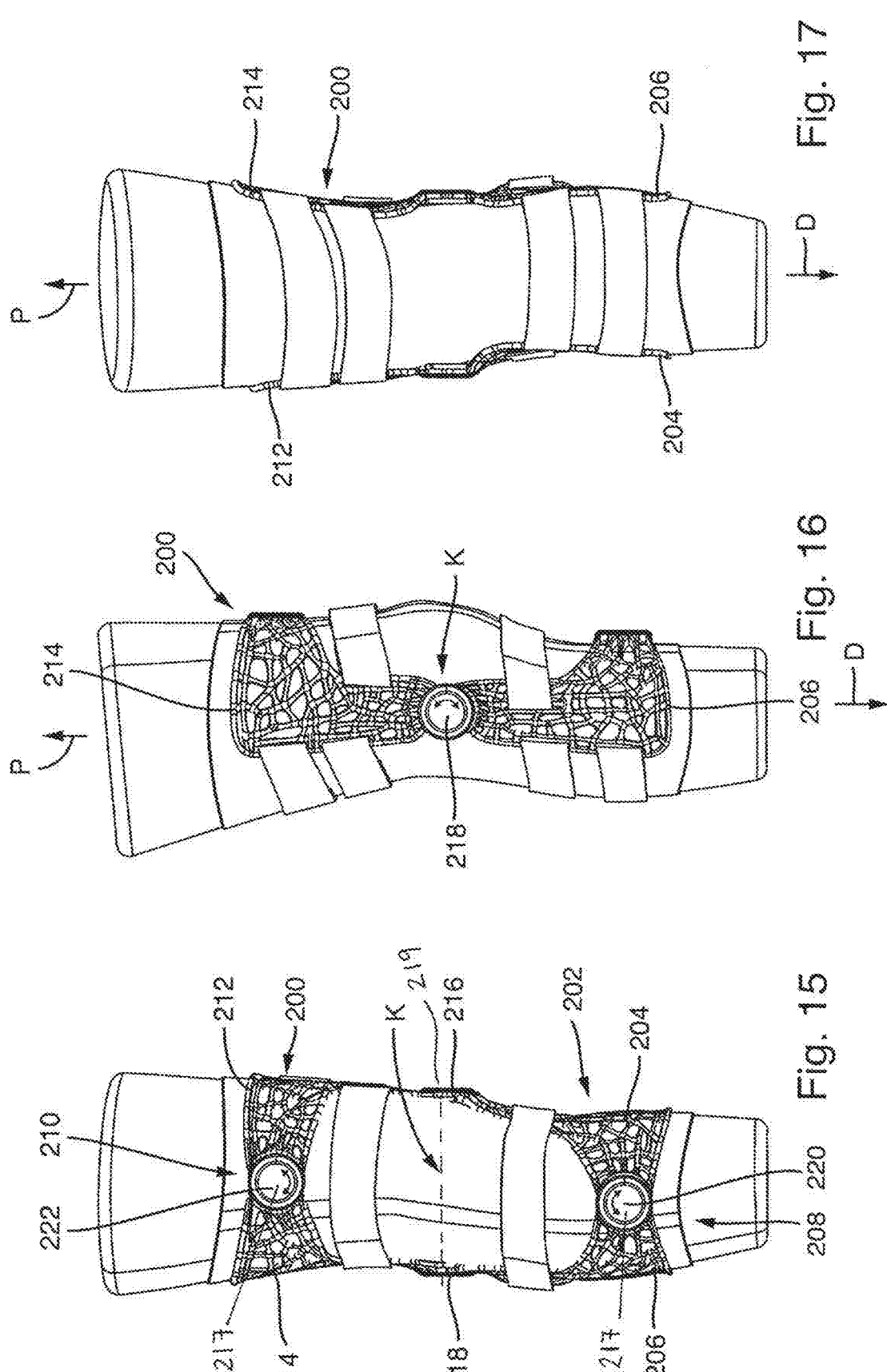
FIG. 15 shows the knee orthosis in a front view.
FIG. 16 shows the knee orthosis in a side view.
FIG. 17 shows the knee orthosis in a rear view.
Figure 18:
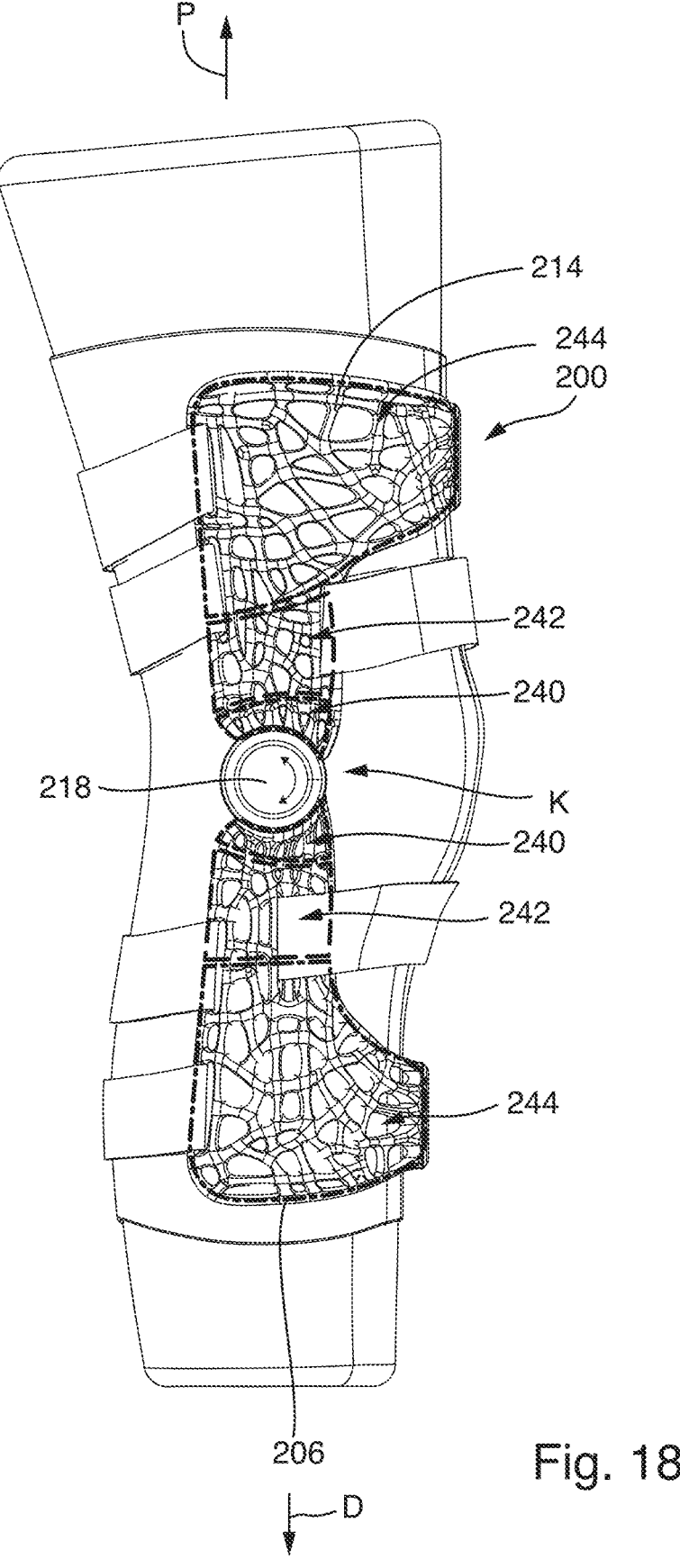
FIG. 18 shows the knee orthosis in a side view.
Figure 19:
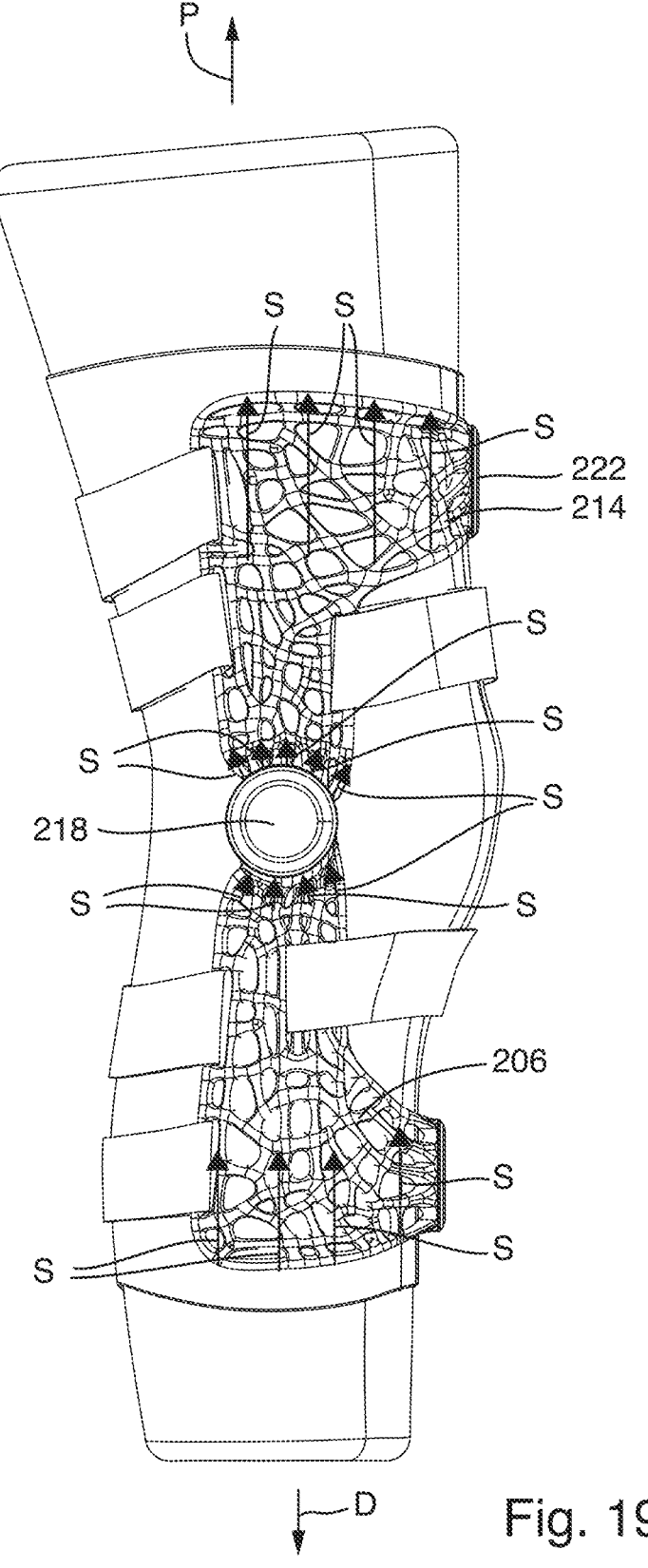
FIG. 19 shows the knee orthosis in a side view.
Figure 20:
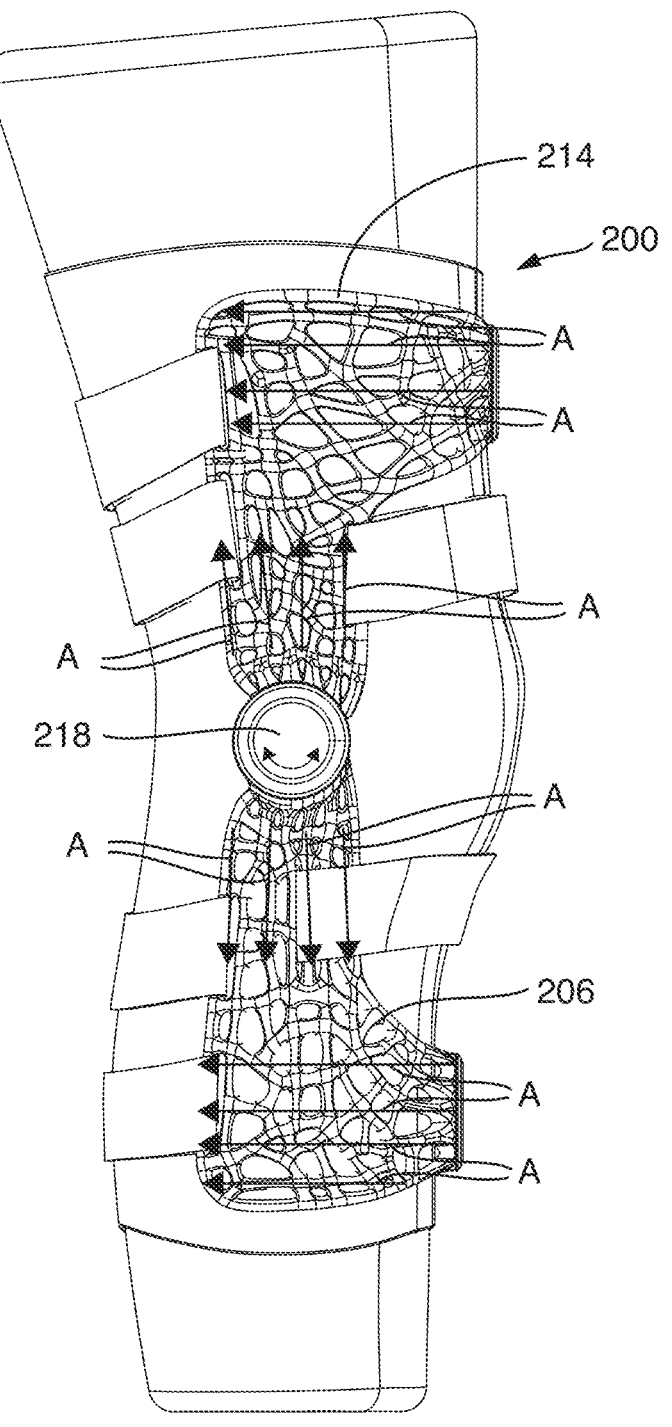
FIG. 20 shows the knee orthosis in a side view.
Figures 21, 22:
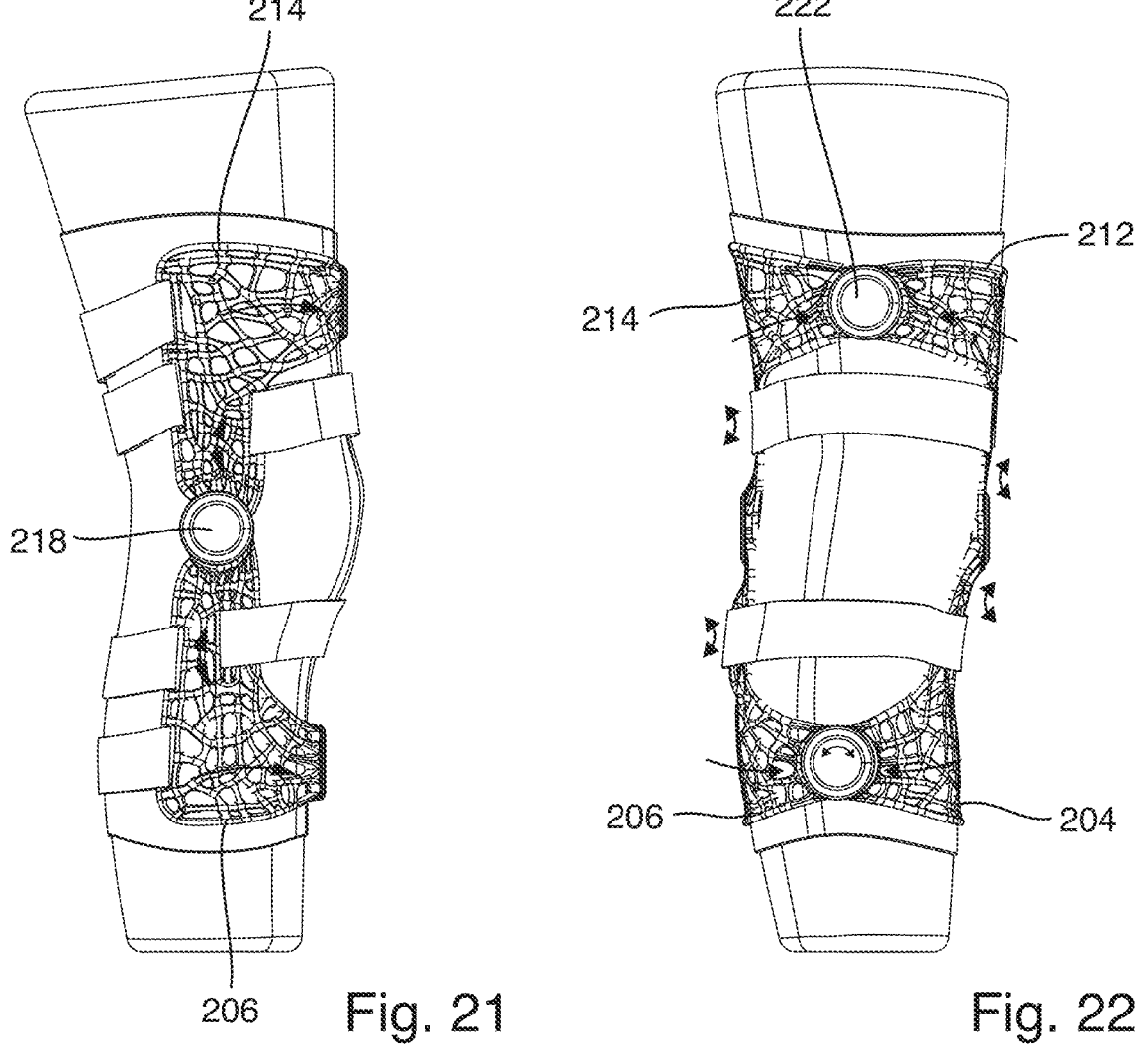
FIG. 21 shows the knee orthosis with marked bending directions.
FIG. 22 shows the knee orthosis with marked bending directions.

FIGS. 15-17 show a knee orthosis 200 according to the invention in an applied state. FIG. 15 shows the knee orthosis 200 when looking at the front side of the knee. FIG. 16 in a side view and in FIG. 17 in a rear view. FIG. 18 shows the knee orthosis 200 in a representation corresponding to FIG. 16, wherein adaptable and stabilizing regions are marked. Corresponding adaptation directions A and stabilization directions S are shown in FIGS. 19 and 20. FIGS. 21 and 22 show the bendability of the adaptable regions and the stabilizing effect of the stabilizing regions.

The knee orthosis 200 comprises a stability-providing structure 202. The stability-providing structure 202 comprises a first structural component 204 and a second structural component 206, both of which are arranged on a distal side 208. A third structural component 212 and a fourth structural component 214 are arranged on the proximal side 210 of the knee orthosis 200. The individual structural components are connected to one another via several articulations.

A first (laterally arranged) articulation 216 and a second (laterally arranged) articulation 218 are arranged at the level of the bending axis of the knee joint K of the wearer of the knee orthosis 200 (relative to the provided applied state of the orthosis). These articulations each connect a structural component 204, 206 arranged on the distal side 208 to a structural component 212, 214 arranged on the proximal side.

The first structural component 204 is connected to the second structural component 206 via a third articulation 220. The two structural components arranged on the proximal side, i.e., the third structural component 212 and the fourth structural component 214, are connected to one another via a fourth articulation 222.

The first articulation 216 and the second articulation 218 enable a bending of the knee with the knee orthosis 200 applied. The third articulation 220 and the fourth articulation 222 enable the orthosis to bear tightly against the body in cooperation with the local flexibility of the stabilizing structure 202. In particular, the first (laterally arranged) articulation 216 and the second (laterally arranged) articulation 218 can be brought directly into contact with the knee. For this purpose, the position of the respective structural components connected thereby can be adapted via the third articulation 220 and the fourth articulation 222. The fourth articulation 222 thus allows an adaptation of the angular position between the third structural component 212 and the fourth structural component 214. Accordingly, the third articulation 220 enables an adaptation of the position of the first structural component 204 relative to the second structural component 206.

In FIG. 18, stabilizing regions 240 and adaptable regions 242 on the second structural component 206 and the fourth structural component 214 are illustrated; the two other structural components have a corresponding arrangement of the individual adaptable and stabilizing regions. The two structural components also each have mixed regions 244 in which the structural components on the one hand are designed to be bendable in one direction and flexibly adaptable to the body shape and, on the other hand, are stiff and stabilizing in another direction. The stabilization directions S are illustrated in FIG. 19 and the adaptation directions A in FIG. 20.

FIGS. 21 and 22 illustrate the possible elastic deformation movements on the structural components. Starting from the articulation 218, a flexurally rigid region is connected in the proximal direction by the orthosis being rigid. Further in the proximal direction P, an adaptable region follows in which the structural component 214 is flexible. The flexibility in this region is used to compensate for a movement in the fourth articulation 222. A partially rigid and partially flexible region 244 is arranged following this region. In this region, the structural component 214 can be adapted with respect to its curvature with which it is placed around the leg of a wearer. However, a bendability in other directions is not provided. As a result, i.e., due to the adaptability to the circumference of the leg of a wearer, as well as the flexibility provided by the fourth articulation 222 and the adaptable region 242, the knee orthosis 200 can be very tightly applied to the body. The structural component 206 has a corresponding sequence of a stiff or stabilizing region 240 and, following thereon in the distal direction, an adaptable region 242 and a partially flexible region 244 (FIG. 18).

The invention claimed is:

1. An orthosis (10, 110, 200) comprising a stability-providing structural component (18, 20, 101, 102, 103, 204, 206, 212, 214), the stability-providing structural component (18, 20, 101, 102, 103, 204, 206, 212, 214) having an irregular lattice structure (47, 147) over its entire surface, the irregular lattice structure (47, 147) having webs (48, 148) made of strengthening structural material, and the webs (48, 148) delimiting irregularly shaped recesses (52, 152) free of structural material, the stability-providing structural component (18, 20, 101, 102, 103, 204, 206, 212, 214) having a planar design and having at least one stabilization direction (S) lying in a planar extension (43), transverse to which the stability-providing structural component (18, 20, 101, 102, 103, 204, 206, 212, 214) is designed to have stabilizing flexural rigidity in order to stabilize a limb of a wearer of the orthosis (10, 110, 200), characterized by the stability providing structural component (18, 20, 101, 102, 103, 204, 206, 212, 214) has one or more stabilizing regions (40, 140, 240) and one or more adaptable regions (42, 142, 242); the webs (48, 148) have a predominant part in the one or more stabilizing regions (40, 140, 240) and a corresponding predominant part of the webs (48) in the one or more adaptable regions (42, 142, 242); the predominant part in the one or more stabilizing regions (40, 140, 240) has a material thickness that is at least twice as thick as the corresponding predominant part in the one or more adaptable regions (42, 142, 242); and the stability-providing structural component (18, 20, 101, 102, 103, 204, 206, 212, 214) has an adaptation direction (A) lying in the planar extension (43), transversely to which the stability-providing structural component (18, 20, 101, 102, 103, 204, 206, 212, 214) has a locally bendable design, so that the orthosis can be brought into planar contact with a contour of a limb of a wearer of the orthosis (10, 110, 200) by bending transverse to the adaptation direction (A).

2. The orthosis (10, 110, 200) according to claim 1, characterized by the stability-providing structural component (18, 20, 101, 102, 103, 204, 206, 212, 214) is connected to at least one fastening strap (16, 116), which is fastened, detachably, in a fixed extension direction (174) on the stability-providing structural component (18, 20, 101, 102, 103, 204, 206, 212, 214), and is designed for a circular wrapping of the limb of the wearer of the orthosis (10, 110, 200) that is to be stabilized by the orthosis (10, 110, 200), the circular wrapping being carried out by the at least one fastening strap (16, 116) by itself or by the at least one fastening strap (16, 116) and at least one stability-providing structural component (18, 20, 101, 102, 103, 204, 206, 212, 214) of the orthosis (10, 110, 200) in conjunction with the at least one fastening strap (16, 116).

3. The orthosis (10, 110, 200) according to claim 2, characterized by the stability-providing structural component (18, 20, 101, 102, 103, 204, 206, 212, 214) has one or more stabilizing regions (40, 140, 240) and one or more adaptable regions (42, 142, 242), the stability-providing structural component (18, 20, 101, 102, 103, 204, 206, 212, 214) comprising at least one adaptable region (42, 142, 242) which, when viewed along the stabilization direction (S) in the one or more stabilizing regions (40, 140, 240), is arranged next to the at least one stabilizing regions (40, 140, 240), the one or more adaptable regions (42, 142, 242) next to the one or more stabilizing regions (40, 140, 240) which are each adaptable on both sides being arranged on both sides of the one or more stabilizing regions (40, 140, 240) when viewed along the stabilization direction (S) in the one or more stabilizing regions.

4. The orthosis (10, 110, 200) according to claim 2, characterized by the orthosis comprises two structural components (18, 20, 101, 102, 103, 204, 206, 212, 214) which are each integrally formed in one piece.

5. The orthosis (10, 110, 200) according to claim 2, characterized by a pliable padding component (14) is arranged on a side of the structural component (18, 20, 101, 102, 103, 204, 206, 212, 214) provided for contacting the limb of the wearer and is detachably or non-detachably connected to the stability-providing structural component (18, 20, 101, 102, 103, 204, 206, 212, 214).

6. The orthosis (10, 110, 200) according to claim 2, characterized by the stability-providing structural component (18, 20, 101, 102, 103, 204, 206, 212, 214) is produced as a one-piece injection-molded part.

7. The orthosis (200) according to claim 2, characterized by the orthosis (200) is a knee orthosis (200) and comprises a plurality of stability-providing structural components (204, 206, 212, 214) connected to one another in an articulated manner, a proximal portion of the stability-providing structure (202) being pivotably connected in the applied state to a distal portion via articulations (216, 218) arranged on both sides next to the knee of the wearer, the proximal and distal portions each comprising two stability-providing structural components (204, 206, 212, 214) which are adaptable relative to one another via a distal and a proximal articulation (220, 222), the proximal articulation (222) and the distal articulation (220) allowing a pivoting movement about an axis which runs orthogonally with respect to the pivot axis of the articulations at the height of the knee joint, which articulations connect the proximal portion to the distal portion.

8. The orthosis (10, 110, 200) according to claim 1, characterized by the orthosis comprises two stability-providing structural components (18, 20, 101, 102, 103, 204, 206, 212, 214) which are each integrally formed in one piece.

9. The orthosis (10, 110, 200) according to claim 8, characterized by the two stability-providing structural components (18, 20, 101, 102, 103, 204, 206, 212, 214) are pivotably connected to one another via an articulation (25, 216, 218, 220, 222).

10. The orthosis (10, 110, 200) according to claim 9, characterized by the two stability-providing structural components (18, 20, 101, 102, 103, 204, 206, 212, 214) are connected to one another via a connecting device (20, 120) in a fixed relative position and orientation and are fixed in relation to one another.

11. The orthosis (10, 110, 200) according to claim 8, characterized by the two stability-providing structural components (18, 20, 101, 102, 103, 204, 206, 212, 214) are connected to one another via a connecting device (20, 120) in a fixed relative position and orientation and are fixed in relation to one another.

12. The orthosis (200) according to claim 1, characterized by the orthosis (200) is a knee orthosis (200) and comprises a plurality of stability-providing structural components (204, 206, 212, 214) connected to one another in an articulated manner, a proximal portion of the stability-providing structure (202) being pivotably connected in an applied state to a distal portion via articulations (216, 218) arranged on both sides next to the knee of the wearer, the proximal and distal portions of the stability-providing structure (202) each comprising two stability-providing structural components (204, 206, 212, 214) which are adaptable relative to one another via a distal and a proximal articulation (220, 222), the proximal articulation (222) and the distal articulation (220) allowing a pivoting movement about an axis (217) which runs orthogonally with respect to a pivot axis (219) of the articulations at a height of the knee joint, which articulations connect the proximal portion to the distal portion.

13. The orthosis according to claim 12, characterized by an inclination of the proximal portion and the distal portion is adaptable to the two stability-providing structural components (204, 206, 212, 214), which are arranged running proximally to distally, via the proximal articulation (222) and the distal articulation (220), and the two stability-providing structural components (204, 206, 212, 214), in order to be able to compensate for this inclination adaptation, having a bendable adaptable region (242), which, by means of a stabilizing region (240), is spaced apart from a respective articulation (220, 222) and configured to be at the height of the knee joint that pivotably connects the proximal portion to the distal portion.

14. The orthosis (110) according to claim 1, characterized by the orthosis (110) is a wrist orthosis (110) and has a wrist support portion formed by a structural component (101) or is part of the structural component (101), the structural component (101) having a stabilizing region (140) extending from proximal to distal direction and extending in an intended applied state up to the wrist, adaptable regions (142) curved in a circumferential direction being arranged to the left and right of the stabilizing region (140) when viewed in the distal direction (D) and being configured to be flexibly adaptable to an arm diameter of the wearer, the stabilization direction (S) extending in the stabilizing region (140) in the proximal-to-distal direction, and the adaptation direction (A) of any adaptable regions (142) that may be present extending in the arm circumferential direction in relation to the intended applied state of the orthosis.

15. The orthosis (110) according to claim 14, characterized by the orthosis (110) comprises a finger rest, which is formed as a further structural component (102) or part of the structural component (101) that forms the wrist support portion, the orthosis (110) alternatively or additionally comprising a thumb rest formed as a further structural component (103) or part of the structural component (101) forming the wrist support portion.

16. The orthosis (10) according to claim 1, characterized by the orthosis (10) is an ankle orthosis (10) and on a distal side has two shell elements (24), which are designed to contact a foot of a wearer in each case on a lateral and foot sole side, and which can be fixed in a variable position relative to one another, the shell elements (24) being pivotably connected to a respective structural component (18) of a plurality of stability-providing structural components via an articulation (25) arranged proximally on the shell elements (24), the respective structural component (18) extending from the articulation (25) in a proximal direction (P).

17. The orthosis (10) according to claim 16, the preceding claim, characterized by the respective stability-providing structural component (18) extending in the proximal direction (P) from the articulation (25) comprises a central stabilizing region (140) running in the distal-to-proximal direction, the stabilization direction (S) of which extends in the distal-to-proximal direction, the orthosis (10) in the applied state further comprising adaptable regions (42) arranged laterally from the stabilizing region (40) when viewed in the distal-to-proximal direction, the adaptation direction (A) of said stability-providing structural component running in a circumferential direction of the lower leg of the wearer.

18. The orthosis (10, 110, 200) according to claim 1, characterized by the stability-providing structural component (18, 20, 101, 102, 103, 204, 206, 212, 214) comprising at least one adaptable region (42, 142, 242) which, when viewed along the stabilization direction (S) in the one or more stabilizing regions (40, 140, 240), is arranged next to the at least one stabilizing regions (40, 140, 240), the one or more adaptable regions (42, 142, 242) next to the one or more stabilizing regions (40, 140, 240) which are each adaptable on both sides being arranged on both sides of the one or more stabilizing regions (40, 140, 240) when viewed along the stabilization direction (S) in the one or more stabilizing regions.

19. The orthosis (10, 110, 200) according to claim 1, characterized by a pliable padding component (14) is arranged on a side of the stability-providing structural component (18, 20, 101, 102, 103, 204, 206, 212, 214) provided for contacting the limb of the wearer and is detachably or non-detachably connected to the stability-providing structural component (18, 20, 101, 102, 103, 204, 206, 212, 214).

20. The orthosis (10, 110, 200) according to claim 1, characterized by the stability-providing structural component (18, 20, 101, 102, 103, 204, 206, 212, 214) is produced as a one-piece injection-molded part.

* * * * *